United States Patent [19]

Chu

[11] Patent Number: 4,845,063

[45] Date of Patent: * Jul. 4, 1989

[54] ZEOLITE CATALYST OF IMPROVED HYDROTHERMAL STABILITY

[75] Inventor: Pochen Chu, West Deptford, N.J.

[73] Assignee: Mobil Oil Corporation, New York, N.Y.

[*] Notice: The portion of the term of this patent subsequent to Aug. 26, 2003 has been disclaimed.

[21] Appl. No.: 707,631

[22] Filed: Mar. 4, 1985

Related U.S. Application Data

[62] Division of Ser. No. 585,615, Mar. 5, 1984, abandoned, which is a division of Ser. No. 434,442, Oct. 15, 1982, abandoned.

[51] Int. Cl.$^4$ .......................... B01J 29/28; B01J 37/08
[52] U.S. Cl. .......................... 502/60; 502/64; 502/71; 502/85
[58] Field of Search .......................... 502/60, 64, 71, 77, 502/78, 85

[56] References Cited

U.S. PATENT DOCUMENTS

| | | | |
|---|---|---|---|
| 3,013,985 | 12/1961 | Breck et al. | 502/78 X |
| 3,097,115 | 7/1963 | Moos | 502/64 X |
| 4,276,438 | 6/1981 | Chu | 585/467 |

Primary Examiner—Carl F. Dees
Attorney, Agent, or Firm—Alexander J. McKillop; Michael J. Gilman; Malcolm D. Keen

[57] ABSTRACT

The hydrothermal stability of zeolites is improved by incorporating Group IB metal cations preferably Ag into the zeolite. The improved stability is useful in processes in which the zeolite is frequently exposed to water vapor at elevated temperature, for example, in processes where water is produced in the reaction or in the catalyst regeneration.

24 Claims, 1 Drawing Sheet

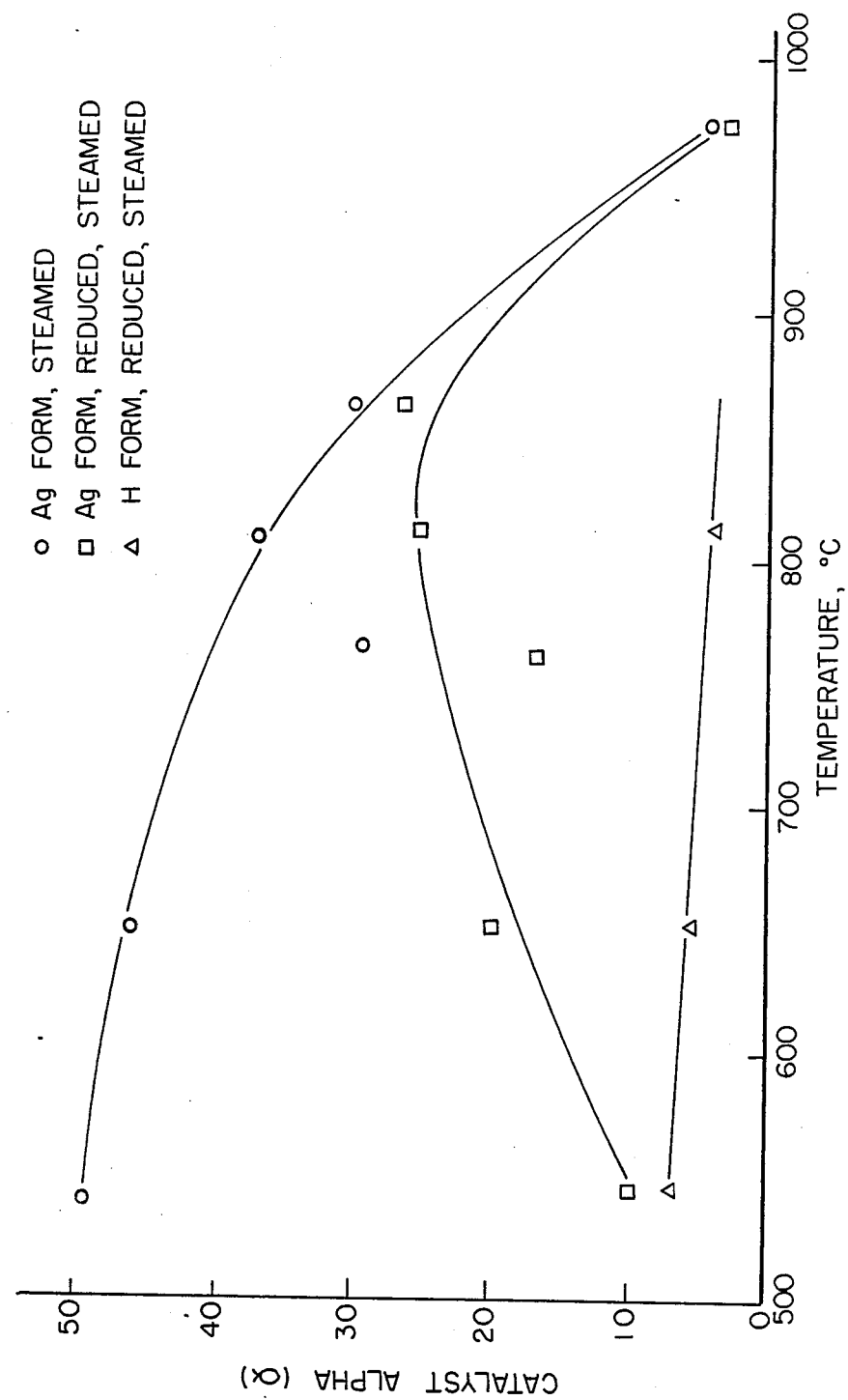

ZEOLITE CATALYST OF IMPROVED HYDROTHERMAL STABILITY

This is a divisional of copending application Ser. No. 585,615, filed on Mar. 5, 1984. Ser. No. 585,615 was a divisional of application Ser. No. 434,442, filed Oct. 15, 1982 and both abandoned.

FIELD OF THE INVENTION

The present invention relates to zeolitic catalysts of improved hydrothermal stability and to a process for making them.

BACKGROUND OF THE INVENTION

Zeolite catalysts have been used and proposed for use in a number of different petroleum refining processes such as cracking, for example, as described in U.S. Pat. Nos. 3,700,585 and 3,907,663, hydrocracking as described in U.S. Pat. No. 3,923,641, dewaxing and hydrodewaxing as described in U.S. Pats. Nos. Re. 28,398, 3,700,585, 3,956,102, 4,110,056 and 3,755,138, aromatization processes of the kind described in U.S. Pats. Nos. 3,806,443, 3,767,568, 3,753,891, 3,770,614 and 3,843,740 and alkylation as described in U.S. Pat. No. 3,641,177. They have also found utility in the petrochemical industry, for example, in alkylation processes of the kind described in U.S. Pat. Nos. 3,668,264, 3,251,897, 4,117,024, 4,049,738 and 4,086,287, isomerization processes of the kind described in U.S. Pats. Nos. 4,100,214 and 4,101,596 and disproportionation processes as described, for example, in 4,106,788 and 3,856,871. Their use in the production of hydrocarbons from other materials such as synthesis gas, methanol, dimethyl ether (DME) or other oxygenated materials is described, for example, in U.S. Pat. Nos. 3,894,102 to 3,894,107, 3,899,544, 4,039,600, 4,048,250 and 4,035,430. In these processes various kinds of zeolites may be used either alone or in combination with one another or with other catalytic materials. Zeolites may be characterized as being small pore materials such as erionite or zeolite A; large pore materials such as zeolite X, zeolite Y or mordenite and the so-called shape selective zeolites exemplified by the ZSM-5 family including ZSM-5 itself, ZSM-11, ZSM-12, ZSM-23, ZSM-35 and ZSM-38.

One problem which has persisted with zeolitic catalysts is that of hydrothermal stability. In many of the processes in which they are used, the zeolites are exposed to water vapor at elevated temperatures and this may tend to reduce the activity of the zeolite by reason of the loss of acidic sites through dehydroxylation and dealuminization, the loss being manifested by a decrease of the alpha value of the zeolite. In some cases, particularly with zeolites of low silica:alumina ratio, crystallinity may be adversely affected. Different zeolites exhibit different degrees of hydrothermal stability but the problem is encountered to some extent with all of them. The exposure to the water vapor may occur during the process itself or in an ancillary treatment step. For example, in the hydrocarbon synthesis processes of the kind described in U.S. Pat. Nos. 3,894,102 to 3,894,107, 3,899,544 and 4,035,430 using oxygenated precursors such as methanol or DME, large amounts of water are produced as by-products of the synthesis and under the reaction conditions commonly employed this will be evolved as steam which will come into direct contact with the catalyst, to its ultimate detriment. In other processes such as catalytic cracking, the steam stripping which is used to remove occluded hydrocarbons prior to regeneration, will obviously produce a similar effect, as will any steam which is present in the regeneration and which has been produced either by combustion of any hydrocarbon material on the catalyst itself or by the combustion of hydrocarbon fuel used to heat the regenerator. Obviously, the deleterious effect of the steam becomes more pronounced the longer and more frequent the exposure to it is; processes in which the catalyst is continuously or continually exposed to steam therefore present greater problems than those where the contact is occasional or at very long intervals. For example, in fluid catalytic cracking (FCC) units the catalyst is continuously circulated through the reactor and the regenerator and comes into contact with steam during each complete cycle when the catalyst is subjected to the stripping and regeneration steps. Conversely, processes in which the exposure to steam is infrequent, e.g. the alkylation process of U.S. Pat. No. 4,276,438 where regeneration is carried out about once a year, usually present few problems of hydrothermal stability, at least when water is not one of the by-products of the reaction.

Attempts to improve the hydrothermal stability of zeolites have often been made and have met with varying success; although it has often been found possible to improve the hydrothermal stability, other properties of the zeolite may be adversely affected. For example, various cationic forms of the zeolite such as the rare earth form of the faujasites zeolites have greater hydrothermal stability but the activity of the zeolite in the rare earth form may not be as great as it would be in other forms, and it may not always be practicable or possible to improve the hydrothermal stability in this way. For example, the rare earth cations do not readily enter the structure of the ZSM-5 type zeolites because of the low ion exchange selectivity of these cations. It would therefore be desirable to find a way of improving the hydrothermal stability of these and other zeolites.

SUMMARY OF THE INVENTION

It has now been discovered that the hydrothermal stability of zeolites may be improved by incorporating a metal of Group IB of the Periodic Table, preferably silver into the zeolite. The Periodic Table is the table approved by IUPAC and the U.S. National Bureau of Standards and shown, for example, in the Periodic Chart of the Fisher Scientific Company, Catalog No. 5-702-10. According to the present invention, the zeolite is loaded with the group IB metal form and is then used in a process in which it is continually or continuously subjected to exposure to steam, for example, in fluid catalytic cracking or oxygenate-to-hydrocarbon conversion.

DRAWINGS

The single FIGURE of the accompanying drawings is a graph showing the effect of calcination temperature on zeolites.

DESCRIPTION OF PREFERRED EMBODIMENTS

A wide variety of porous zeolites may be treated by the present stabilization method but the process is especially useful with the large pore zeolites such as zeolite beta and the zeolites of the ZSM-5 type which have a structural silica:alumina ratio of at least 12:1 and a Constraint Index of 1 to 12. The stabilization has been found to be less effective with the small pore zeolites such as erionite and zeolite A which have pore sizes of less than 5 Angstroms. Large pore zeolites which may be exchanged into the Group IB metal form have pore dimensionsn of at least 5 Angstroms and include, for example, zeolite ZSM-20, zeolite X, zeolite Y, zeolite beta and mordenite. The ZSM-5 type zeolites typically have at least one pore dimension from 5 Angstroms to 6 Angstroms but they are more readily characterized by their Constraint Index.

The measuring and significance of the term "Constraint Index" are described in U.S. Pat. No. 4,016,218, to which reference is made for details of the method by which the index is deterined and examples of its values for typical zeolite. The Constraint Index is a measure of the extent to which the crystal structure of the zeolite provides restricted access to the internal structure of the zeolite. To this extent, the Constraint Index is related to structure even though its measurement is dependent upon a test which exploits the cracking activity of the zeolite, a property which is in turn dependent upon the possession of acidic sites and acidic functionality by the zeolite. The zeolite sample selected for use in the measurement of the Constraint Index should therefore be representative of the structure of the zeolite whose Constraint Index is to be measured in addition to possessing sufficient cracking activity for the determination to be made. The preferred zeolites having constraint indices within the range of 1 to 12 are ZSM-5, ZSM-11, ZSM-12, ZSM-35 and ZSM-39. The preferred zeolites of this kind as mentioned above, have constraint indices from 1 to 12, indicating that they have structures which provide controlled but not unimpeded access for larger hydrocarbon molecules to the internal structure of the zeolite.

ZSM-5 is described in U.S. Pat. No. 3,702,886; ZSM-11 in U.S. Pat. No. 3,709,979; ZSM-12 in U.S. Pat. No. 3,832,449; ZSM-23 in U.S. Pat. No. 4,076,842; ZSM-35 in U.S. Pat. No. 4,016,245 and ZSM-38 in U.S. Pat. No. 4,046,859, and reference is made to these patents for details of these zeolites, their preparation and properties.

Zeolite ZSM-20 is described in U.S. Pat. No. 3,972,983 and 4,021,331 and zeolite beta in U.S. Pat. Nos. 3,303,069 and Re. 28,341; reference is made to these patents for details of these zeolites, their preparation and properties.

When zeolites are prepared in the presence of organic cations they are initially catalytically inactive, possibly because the intracrystalline free space is occupied by organic cations from the forming solution. They may be activated by heating in an inert atmosphere at 540° C. for at least about one hour, for example, followed by base exchange with ammonium salts followed by calcination at 540° C. in air. The presence of organic cation in the forming solution may not be absolutely essential to the formation of the zeolite but these cations do appear to favor the formation of the desired crystal structure.

The zeolite is loaded with the Group IB metal in cationic form. The metal may be incorporated into the zeolite by ion-exchange or by impregnation but it has been found that whichever method is used, the metal should be in its cationic form. When the metal is introduced by ion exchange from a solution containing cations of the metal, it will obviously be in the desired form and for this reason, ion exchange is the preferred method of incorporating the metal. On the other hand, if the metal is incorporated into the zeolite by impregnation, it must be converted to the desired cationic form. For example, if the metal is impregnated into the zeolite using a solution of an anionic complex of the metal such as $[CuCl_4]^{2-}$ and $[Ag(CN)_4]^{3-}$, the metal must be converted to the cationic form. This may usually be accomplished by oxidation using a suitable oxidizing agent. The complex anion may, if desired, be first converted to the zerovalent metal e.g. by heating and the metal then oxidized to the required cationic form, e.g. by heating in an oxidizing atmosphere. Similarly, if the cationic form of the metal becomes reduced during use it may be re-oxidized to the cationic form so as to retain the desired stability. Suitable oxidizing treatment for silver is to use an oxidizing atmosphere of oxygen of air at 400° C. to 600° C., preferably 480° C. to 540° C.

The zeolite may be converted to the Group IB metal form by conventional base exchange techniques using, for example, an aqueous solution of the cation of the metal. When the metal cation being introduced into the zeolite is silver, solutions of silver nitrate are useful and preferred. If the metal cation is copper, solutions of copper chloride, copper sulfate or copper nitrate may be used and if the metal cation is gold, solutions of gold chloride are suitable. Methods of incorporating Group IB metals into zeolites of the ZSM-5 type are described in U.S. Pat. No. 4,276,43 and reference is made to that patent for details of such methods and of suitable compounds of Group IB metals for this purpose. Similar cation exchange methods may be employed with other zeolites such as zeolite beta.

Conventional impregnation techniques such as by impregnation with solutions of complex metal anions which may be used for introducing the metal in this way as an alternative to exchange with the metal cations.

The metal content of the zeolite should normally be at least 0.1 weight percent, regardless of the method of incorporation, and preferably should be at least 0.5 weight percent for satisfactory stabilization. For the preferred class of zeolites described above having Constraint Indices of 1 to 12 the metal content should normally be at least 0.5. The maximum loading will be set by the nature of the zeolite and the method by which the metal is incorporated into the zeolite. If ion exchange is used, the maximum loading will be set by the exchange capacity of the zeolite which, in turn, is a function of silica:alumina ratio and since acidic sites will normally be desired in the zeolite in order to confer activity the proportion of available sites occupied by the metal cations will be appreciably below the total. If the metal is incorporated by impregnation the exchange capacity of the zeolite will impose no fundamental limitation on the loading but other factors e.g. sorption of the metal containing species, may do. The amount of metal incorporated into the zeolite will therefore tend to be of the same order, regardless of the method of incorporation. Generally, the maximum loading will be 10 weight percent and, more usually, not more than 5 weight percent.

The cation exchange with the Group IB metal cations should be sufficient to ensure that 10 percent of the exchangeable sites on the zeolite are in the Group IB metal form and preferably at least 50 percent of the exchangeable sites should be in that form. Exchange to the desired extent can be ensured by conventional techniques such as prolonged exchange, repeated exchange and so on.

It has been found that the degree of improvement in the hydrothermal stability is greater with higher structural silica:alumina ratios in the zeolite. With the large pore zeolites, ratios of at least 30:1 are preferred, especially for zeolite beta and with the ZSM-5 type zeolites (Constraint Index of 1 to 12), ratios of at least 40:1 and preferably even higher, e.g. over 100:1, 200:1 or even 500:1.

If the zeolite selected may be produced in the desired highly siliceous form by direct synthesis, this will often be the most convenient method for obtaining it. Zeolite beta, for example, is known to be capable of being synthesized directly in forms having silica:alumina ratios up to 100:1, as described in U.S. Pat. Nos. 3,308,069 and Re 28,341 which describe zeolite beta, its preparation and properties in detail. Zeolite Y, on the other hand, can be synthesized only in forms which have silica:alumina ratios up to about 5:1 and in order to achieve higher ratios, resort may be made to various techniques to remove structural aluminum so as to obtain a more highly siliceous zeolite. The same is true of mordenite which, in its natural or directly synthesized form has a silica:alumina ratio of about 10:1. Zeolite ZSM-20 may be directly synthesized with silica:alumina ratios of 7:1 or higher, typically in the range of 7:1 to 10:1, as described in U.S. Pat. Nos. 3,972,983 and 4,021,331. Zeolite ZSM-20 also may be treated by various methods to increase its silica:alumina ratio.

Control of the silica:alumina ratio of the zeolite in its as-synthesized form may be exercised by an appropriate selection of the relative proportions of the starting materials, especially the silica and alumina precursors, a relatively smaller quanity of the alumina precursor resulting in a higher silica:alumina ratio in the product zeolite, up to the limit of the synthetic procedure. If higher ratios are desired and alternative syntheses affording the desired high silica:alumina ratios are not available, other techniques such as those described below may be used in order to prepare the desired highly siliceous zeolites.

The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (GA) of ammonia desorption, a low ammonia titration may be obtained if cationic aluminum prevents exchange of the ammonium ions onto the acidic sites. These disparities are particularly troublesome when certain treatments such as the dealuminzation methods described below which result in the presence of ionic aluminum free of the zeolite structure are employed. Due care should therefore be taken to ensure that the framework silica:alumina ratio is correctly determined.

A number of different methods are known for increasing the structural silica:alumina ratio of various zeolites. Many of these methods rely upon the removal of aluminum from the structural framework of the zeolite by chemical agents appropriate to this end. A considerable amount of work on the preparation of aluminum deficient faujasites has been performed and is reviewed in advances in Chemistry Series No. 121, Molecular Sieves, G.T. Kerr, American Chemical Society, 1973. Specific methods for preparing dealuminized zeolites are described in the following, and reference is made to them for details of the method: Catalysis by Zeolites (International Symposium on Zeolites, Lyon, Sept. 9–11, 1980), Elsevier Scientific Publishing Co., Amsterdam, 1980 (dealuminization of zeolite Y with silicon tetrachloride); U.S. Pat. No. 3,442,795 and G.B. No. 1,058,188 (hydrolysis and removal of aluminum by chelation); G.B. No. 1,061,847 (acid extraction of aluminum); U.S. Pat. No. 3,493,519 (aluminum removal by steaming and chelation); U.S. Pat. No. 3,591,488 (aluminum removal by steaming); U.S. Pat. No. 4,273,753 (dealuminization by silicon halides and oxyhalides); U.S. Pat. No. 3,691,099 (aluminum extraction with acid); U.S. Pat. No. 4,093,560 (dealuminization by treatment with salts); U.S. Pat. No. 3,937,791 (aluminum removal with Cr(III) solutions); U.S. Pat. No. 3,506,400 (steaming followed by chelation); U.S. Pat. No. 3,640,681 (extraction of aluminum with acetylacetonate followed by dehydroxylation); U.S. Pat. No. 3,836,561 (removal of alumnium with acid); DE-OS No. 2,510,740 (treatment of zeolite with chlorine or chlorine-contrary gases at high temperatures), NL No. 7,604,264 (acid extraction), JA No. 53,101,003 (treatment with EDTA or other materials to remove aluminum) and J. Catalysis 54 295 (1978) (hydrothermal treatment followed by acid extraction).

Because of their convenience and practicality the preferred dealuminization methods for preparing the present highly siliceous zeolites are those which rely upon acid extraction of the aluminum from the zeolite. Zeolite beta may be dealuminized by acid extraction using mineral acids such as hydrochloric acid and highly siliceous forms of zeolite Y may be prepared steaming or by acid extraction of structural aluminum (or both) but because zeolite Y in its normal, as-synthesized condition, is unstable to acid, it must first be converted to an acid-stable form. Methods for doing this are known and one of the most common forms of acid-resistant zeolite Y is known as "Ultrastable Y" (USY); it is described in U.S. Pat. Nos. 3,293,192 and 3,402,996 and the publication, Society of Chemical Engineering (London) Monograph Molecular Sieves, page 186 (1968) by C. V. McDaniel and P. K. Maher, and reference is made to these for details of the zeolite and its preparation. In general, "ultrastable" refers to Y-type zeolite which is highly resistant to degradation of crystallinity by high temperature and steam treatment and is characterized by a $R_2O$ content (wherein R is Na, K or any other akali metal ion) of less than 4 weight percent, preferably less than 1 weight percent, and a unit cell size less than 24.5 Angstroms and a silica to alumina mole ratio in the range of 3.5 to 7 or higher. The ultrastable form of Y-type zeolite is obtained primarily by a substantial reduction of the alkali metal ions and the unit cell size reduction of the alkali metal ions and the unit cell size reduction. The ultrastable zeolite is identified both by the smaller unit cell and the low alkali metal content in the crystal structure.

The ultrastable form of the Y-type zeolite can be prepared by successively base exchanging a Y-type zeolite with an aqueous solution of an ammonium salt, such as ammonium nitrate, until the alkali metal content of the Y-type zeolite is reduced to less than 4 weight percent. The base exchanged zeolite is then calcined at a temperature of 540° C. to 800° C. for up to several hours, cooled and successively base exchanged with an aqueous solution of an ammonium salt until the alkali metal content is reduced to less than 1 weight percent, followed by washing and calcination again at a temperature of 540° C. to 800° C. produce an ultrastable zeolite Y. The sequence of ion exchange and heat treatment results in the substantial reduction of the alkali metal content of the original zeolite and results in a unit cell shrinkage which is believed to lead to the ultra high stability of the resulting Y-type zeolite.

The ultrastable zeolite Y may then be extracted with acid to produce a highly siliceous form of the zeolite.

Other methods for increasing the silica:alumina ratio of zeolite Y by acid extraction are described in U.S. Pat. No. 4,218,307, 3,591,488 and 3,691,099, to which reference is made for details of these methods.

Zeolite ZSM-20 may be converted to more highly siliceous forms by a process similar to that used for zeolite Y: first, the zeolite is converted to an "ultrastable" form which is then dealuminized by acid extraction. The conversion to the ultrastable form may be suitably be carried out by the same sequence of steps used for preparing ultrastable Y. The zeolite is successively base-exchanged to the ammonium form and calcined, normally at temperatures above 700° C. The calcination should be carried out in a deep bed in order to impede removal of gaseous products, as recommended in Advances in Chemistry Series, No. 121, op cit. Acid extraction of the "ultrastable" ZSM-20 may be effected in the same way as described above for zeolite beta.

Highly siliceous forms of mordenite may be made by acid extraction procedures of the kind described, for example, in U.S. Pat. Nos. 3,691,099, 3,591,48 and other dealuminization techniques which may be used for mordenite are disclosed, for example, in U.S. Pat. Nos. 4,273,753, 3,493,519 and 3,442,795. Reference is made to these patents for a full description of these processes.

The zeolite may be composited with another material which is resistant to the temperatures and other conditions employed in the process. Matrix materials include synthetic or naturally occurring substances e.g. inorganic materials such as clay, silica and/or metal oxides. The latter may be either naturally occurring or in the form of gelatinous precipitates or gels including mixtures of silica and metal oxides. Naturally occurring clays can be composited with the zeolite and these clays can be used in the raw state as originally mined or initially subjected to calcination, acid treatment or chemical modification.

The zeolites may also be composited with a porous matrix material, such as silica-alumina, silica-magnesia, silica-zirconia, silica-titania or a ternary composition, such as silica-alumina-thoria, silica-alumina-zirconia, silica-alumina-magnesia or silica-magnesia-zirconia. The matrix may be in the form of a cogel. The relative proportions of finely divided modified zeolite and inorganic oxide gel matrix may vary widely, with the zeolite content ranging from 1 to 99 percent by weigth and more usually in the range of 5 to about 80 percent by weight of the composite.

The zeolite, when in the Group IB metal form, preferably the silver form, exhibits improved hydrothermal stability, that is, it is more resistant to the deleterious effects of exposure to steam (water vapor) at elevated temperatures. The zeolite in this form is therefore useful in catalytic processes in which it is continuously or continually subjected to exposure to steam. Processes of this kind include those in which water in the form of steam is obtained as a by-product of the reaction which is being catalyzed by the zeolite and, on the other hand, those in which the exposure to the steam occurs in an ancillary process such as stripping or regeneration. Exposure of this kind, which quickly brings about a decrease in the activity of the zeolite is to be distinguished from processes where any exposure to steam takes place at extended intervals of time, for example, during the regeneration of a zeolite catalyst used in an alkylation process of the kind described in U.S. Pat. No. 4,276,438 where regeneration takes place at approximately yearly intervals. The proportionately brief exposure to steam which takes place during regeneration at such extended intervals usually works no substantial harm upon the zeolite and is, by contrast, unobjectionable and poses no problem.

The most severe service, in terms of the zeolite's ability to withstand exposure to steam, is encountered in processes where water in the form of steam is continuously encountered as a by-product of the reaction which is being catalyzed by the zeolite. Processes of this kind include, in particular, those in which an oxygenated starting material such as methanol, dimethyl ether (DME) or ethanol is being converted to a hydrocarbon. Processes of this kind are described, for example, in U.S. Pat. Nos. 3,894,102, 3,894,103, 3,894,104, 3,894,105, 3,894,107, 3,899,544, 3,907,915, 4,039,600, 4,048,250, 4,035,430, 3,928,483, 3,998,898, 4,039,600, 4,035,430, 4,188,336 and British Pat. No. 1,495,794 and 1,489,357.

Processes in which the zeolite is continually exposed to water vapor at elevated temperatures also receive a benefit from the present invention. In the catalytic cracking of petroleum, for example, the catalyst is continuously cycled between the reactor (cracker) in which the cracking reactions take place and the regenerator where the accummulated coke is burnt off. The catalyst is stripped by steam between the reactor and the regenerator and in the regenerator itself steam may be present from the combustion of residual amounts of hydrocarbon occluded in the catalyst. Hydrothermal stability of the cracking catalyst is therefore highly desirable as the catalyst undergoes continual exposure to the deactivating effect of the water vapor. Other continuous processes in which the catalyst is repeatedly exposed to steam at short intervals in rapid succession i.e. continually, would also benefit from the use of the present catalyst.

The thermal treatment of the zeolite subsequent to cation exchange into the Group IB metal form is also significant for the stability of the zeolite. The calcination temperature has been found to affect the zeolite in different ways, depending upon the oxidation state of the metal on the zeolite. If the Ag-exchanged zeolite is calcined, the stability generally declines gradually, with the peak being obtained at calcination temperatures of about 540° C. The decline in stability, measured by the alpha value before and after steaming, becomes sharper at calcination temperatures above about 870° C. and such temperatures should therefore be avoided during calcination; temperatures of 500° C. to 700° C. are preferred for calcining the zeolite when in this form. On the other hand, if the Ag-exchanged zeolite is first reduced, for example, by treatment with hydrogen, the stability (as measured by the activity, alpha) exhibits a peak at calcination temperatures from 750° C. to 875° C., with a marked decline at higher values. This temperature range (750° C. to 875° C.) is preferred when the Ag form of the zeolite is used in applications where reducing atmospheres are predominant. By contrast, hydrogen forms of the zeolite exhibit a monotonic decrease with increasing calcination temperature, at a lower level of stability to that of the Ag-exchanged forms of the same zeolite. In all cases, extremely high calcination temperatures above about 900° C. lead to destruction of the acid sites, the crystal structure or both of the zeolite and consequent loss of activity.

The stability of the zeolite may, as mentioned above, conveniently be determined by measuring the cracking activity, alpha, of the zeolite before and after steaming. A method for determining alpha is found in U.S. Pat. No. 4,016,218 and J. Catalysis Vol. VI, 278–287, 966 and reference is made to these for details of the method.

The invention is illustrated by the following Examples.

EXAMPLE 1

Hydrogen forms of zeolites ZSM-5, ZSM-11, ZSM-12 and beta were echanged with 0.1N $AgNO_3$ solution (20 g. g.$^{-1}$ of catalyst) at room temperature for four hours after which the zeolites were washed until the wash water was free of Ag and then the washed zeolite was dried at 110° C. and calcined in air at 540° C. for 3 hours. The Ag-exchanged zeolites were then steamed at 650° C., atmospheric pressure, 100 percent steam for 4 hours.

The cracking activites of the Ag-exchanged zeolites were then determined. The results are shown in Table 1 below together with the results of a similar determination made on the hydrogen forms of the corresponding zeolites both before and after a similar steaming treatment.

TABLE 1

| Hydrothermal Stability of Ag Containing Zeolites | | | | |
|---|---|---|---|---|
| Zeolite Type | ZSM-5 | ZSM-11 | ZSM-12 | Beta |
| $SiO_2/Al_2O_3$ | 70 | 70 | 120 | 30 |
| Cation Form | H H + Ag | H H + Ag | H H + Ag | H H + Ag |
| Alpha Activity, Fresh | 200 200 | 200 200 | 80 80 | 300 300 |
| Alpha Activity, Steamed | 7 49 | 3 33 | 13 23 | 10 67 |

The results in Table 1 show that the Ag forms of the zeolites are more hydrothermally stable than the hydrogen forms.

EXAMPLE 2

In order to demonstrate the Ag metal itself does not contribute to the alpha activity of the catalyst, a low acidity ZSM-5 catalyst zeolite (silica:alumina ratio=20,000:1, extruded with 35% $Al_2O_3$) was exchanged and impregnated with 0.1 N $AgNO_3$ solution at room temperature for four hours to an Ag loading of 1.0 percent. After calcination and steaming in the manner described above, the alpha value was determined. The results are shown in Table 2 below together with those of a comparison zeolite catalyst having a silica:alumina ratio of 70:1.

TABLE 2

| Hydrothermal Stability of Ag ZSM-5 Extrudates | | |
|---|---|---|
| | H Form of ZSM-5 extrudate | |
| Base Material | (65% ZSM-5, | 35% $SiO_2/Al_2O_3$) |
| $SiO_2/Al_2O_3$ of ZSM-5 | 70 | 20,000 |
| Ag Content, % Wt. | 1.0 | 1.0 |
| Alpha Activity, Fresh | 200 | 2 |
| Alpha Activity, Steamed | 30 | 3 |

The results above show that the Ag impregnated form did not show any increase in alpha activity over the hydrogen form, thereby demonstrating the Ag itself does not contribute to alpha activity but only protects the existing activity (the low exchange capacity of the low acidity zeolite prevents substantial Ag exchange so that most of the Ag content is present as impregnated Ag).

EXAMPLE 3

A ZSM-5 extrudate (65% zeolite, 35% alumina) containing Ag-exchanged ZSM-5 (silica:alumina =70:1, 3% Ag, based on the weight of the extrudate) was exposed to a stream of flowig n-hexane at 540° C. for 16 hours to determine the stability of the Ag+ ion towards reduction. The sample treated in this way had an alpha value of 39 after subsequent steaming for 4 hours at 650° C. A similar catalyst not exposed to the n-hexane treatment had an alpha value of 41. Blank runs of extrudate containing the hydrogen form zeolite had alpha values of 7 and 6 respectively, for the hexane treated and untreated materials. The data are summarized in Table 3 below.

TABLE 3

| Hydrothermal Stability of ZSM-5 Extrudate After Hydrocarbon Treat | | |
|---|---|---|
| Base Zeolite | Ag ZSM-5 | HZSM-5 |
| $SiO_2/Al_2O_3$ of ZSM-5 | 70 | 70 |
| Ag Content, % Wt. | 3.0 | 0 |
| Activity, Fresh | 289 | 200 |
| Activity, HC Treated and Steamed | 39 | 6 |
| Activity, Steamed | 41 | 7 |

EXAMPLE 4

The effect of the Ag content was investigated by preparing ZSM-5 extrudates (zeolite silica:alumina ratio 70:1, extrudate 65% zeolite, 35% alumina) and steaming them under various conditions with 100% steam. The alpha activity was determined after the steaming. The Ag form zeolites were prepared by cation exchange of ammonium or hydrogen form zeolites with an 0.N $AgNO_3$ solution at 25° C. for 4 hours, to varying Ag contents. The results are shown in Table 4 below.

TABLE 4

| Hydrothermal Stability of Ag ZSM-5 Extrudates - Effect of Ag Content | | | | | | | | | | | | |
|---|---|---|---|---|---|---|---|---|---|---|---|---|
| Original Cation | $NH_4$ | $NH_4$ | H | H | H | H | $NH_4$ | H | H | H | H | H |
| Ag content, % Weight | 1.5 | 2.1 | 1.0 | 3.2 | 0.84 | 0.64 | 3.8 | 3.2 | 0.64 | 0.84 | 0 | 0 |
| Steaming temp. °C. | 650 | 650 | 650 | 650 | 650 | 650 | 650 | 480 | 480 | 480 | 480 | 650 |
| Steaming press., kPa | 100 | 100 | 100 | 100 | 100 | 100 | 100 | 205 | 205 | 205 | 205 | 100 |
| Steaming time, hours | 4 | 4 | 4 | 4 | 4 | 4 | 4 | 42 | 42 | 48 | 48 | 4 |
| Alpha, Steamed | 49 | 59 | 30 | 54 | 30 | 58 | 43 | 148 | 100 | 86 | 15 | 7 |

EXAMPLE 5

The effect of calcination temperature was investigated by calcining ZSM-5 at various temperatures from 540° C. to 980° C. The ZSM-5 (silica:alumina ratio of 70:1) was used either in the Ag form (0.8% Ag) or the hydrogen form. The alpha activity and surface area were determined after calcination for 3 hours and also after steaming the calcined zeolite for 4 hours at 650° C. in 100% steam. The results are shown in Table 5 below together with the alpha values obtained after subjecting the calcined zeolite to reduction in hydrogen (480° C., 2 hours) and steaming (650° C., 100% steam, 4 hours).

The results are also shown in the attached FIGURE in graphical form.

TABLE 5

| Effect of Calcination on Ag ZSM-5 Extrudates | | | | | | | | | |
|---|---|---|---|---|---|---|---|---|---|
| Ag, Wt. % | 0.8 | | | | | | 0 | | |
| Calcination temp., °C. | 540 | 650 | 760 | 815 | 870 | 980 | 540 | 650 | 815 |
| Alpha | 290 | 228 | 194 | 80 | 57 | 9 | 200 | 128 | 15 |
| Surface Area, m²/g | — | 423 | 326 | 295 | 298 | 220 | — | — | — |
| Alpha Steamed | 49 | 46 | 29 | 37 | 30 | 4 | 7 | 6 | 4 |
| Alpha, Reduced and Steamed | 10 | 19 | 17 | 25 | 26 | 3 | 7 | 6 | 4 |

EXAMPLE 6

Samples of zeolite ZSM-5 (silica:alumina ratio 70:1, no alumina binder) were ion exchanged with solutions of silver and copper ions to give cation loadings of 1.0 and 0.81 weight percent, respectively. The alpha activities of the exchanged zeolites were determined before and after steaming for 4 hours at 650° C. in 100 percent steam. The results are shown below in Table 6 together with the corresponding results obtained with the gold impregnated zeolite and the zeolite in its hydrogen form.

TABLE 6

| Effect of Cations on Stability of ZSM.5i | | | | | |
|---|---|---|---|---|---|
| Cation incorporated | Ag | Cu | Au | Au | H |
| Amount, wt. percent | 1.0 | 0.81 | 3 | 6 | — |
| Method | Exchange | | Impreg. | | — |
| Alpha, fresh | 280 | 211 | 281 | 274 | 280 |
| Alpha, Steamed | 49 | 9 | 7 | 8 | 6 |

EXAMPLE 7

Samples of zeolite ZSM-5 having varying structural silica:alumina ratios and a crystal size form 0.0 to 0.05 microns were ion exchanged with 0.1 N AgNO$_3$ solution using 5 ml of solution per gram of zeolite. The alpha activities of the fresh H-form zeolite (equivalent also to that of the Ag-exchanged zeolite), the steamed H-form zeolite and the steamed, Ag-exchanged zeolite were then determined. The steaming conditions were as in Example 5: 650° C., 4 hours in 100 percent steam. The results shown in Table 7 below demonstrate that the stabilizing effect of the cations is more pronounced at higher zeolite silica:alumina ratios.

TABLE 7

| Effect of zeolite SiO$_2$/Al$_2$O$_3$ ratio on stability | | | | | |
|---|---|---|---|---|---|
| Zeolite SiO$_2$/Al$_2$O$_3$ ratio | 40 | 70 | 140 | 220 | 500 |
| Ag content, wt. percent | 1.8 | 1.7 | 0.84 | 0.54 | 0.29 |
| Alpha activity: | | | | | |
| Fresh H form | 400 | 200 | 59 | 43 | 11 |
| Steamed H. form | 12 | 7 | 7 | 9 | 4 |
| Steamed Ag form | 91 | 56 | 42 | 32 | 10 |
| Percent activity retained by Ag form | 23 | 28 | 71 | 74 | 91 |

EXAMPLE 8

ZSM-5 catalysts were used in the conversion of methanol to hydrocarbons by passing a feed stream containing 83 weight percent methanol over the ZSM-5 catalyst at a pressure of 2170 kPa (300 psig), a reactor inlet temperature of 390° C. and WHSV of 3.2 hr$^{-1}$ at a recycle ratio of 4.5:1 (recycle is principally light gas product, C$_{4-}$).

Two ZSM-5 catalysts were used. Both had silica/alumina ratios of 70:1. One catalyst was HZSM-5 and the other AgZSM-5 produced by ion exchange to an Ag content of 1.01 weight percent.

The reaction was continued in each case to the point that conversion had declined to the same level determined by a methanol content of 0.5 percent in the total conversion product. At this point the catalyst was oxidatively regenerated. The time in days between successive regenerations i.e. the cycle length, is shown in Table 8 below. The AgZSM-5 catalyst has generally longer cycle times indicating that it has superior hydrothermal stability.

TABLE 8

| Aging Test of ZSM-5 | | |
|---|---|---|
| | Cycle Length, Days | |
| Cycle | HZSM-5 | AgZSM-5 |
| 1 | 6.1 | 7.5 |
| 2 | 9.1 | 7.8 |
| 3 | 7.0 | 8.3 |
| 4 | 2.8 | 7.1 |
| 5 | 1.2 | 5.1 |

I claim:

1. A method of hydrothermally stabilizing a crystalline aluminosilicate zeolite having at least one pore dimension of at least 5 Angstroms and a silica:alumina ratio of at least 30:1 and which is a large pore zeolite or a zeolite having a Constraint Index of 1 to 12, which comprises calcining the zeolite containing silver metal cations at a temperature from 540° to 900° C.

2. A method according to claim 1 in which the content of silver cations is at least 0.1 weight percent.

3. A method according to claim 1 in which the content of silver cations is at least 0.5 weight percent.

4. A method according to claim 1 in which the content of silver cations is from 0.5 to 10 weight percent.

5. A method according to claim 1 in which the content of silver cations is from 0.5 to 5 weight percent.

6. A method according to claim 1 in which the zeolite is calcined at a temperature of 540° to 900° C. while containing reduced silver cations.

7. A method according to claim 6 in which the calcination temperature is from 750° to 875° C.

8. A method according to claim 6 in which the zeolite has a Constraint Index of 1 to 12 and a silica:alumina ratio of at least 30.1.

9. A method according to claim 6 in which the zeolite has a Constraint Index of 1 to 12 and a silica:alumina ratio of at least 40:1.

10. A method according to claim 9 in which the content of silver cations is at least 0.1 weight percent.

11. A method according to claim 10 in which the content of silver cations is at least 0.5 weight percent.

12. A method according to claim 11 in which the content of silver cations is from 0.5 to 10 weight percent.

13. A method according to claim 12 in which the content of silver cations is from 0.5 to 5 weight percent.

14. A method according to claim 9 in which the zeolite is ZSM-5.

15. A method of hydrothermally stabilizing a crystalline aluminosilicate zeolite having at least one pore dimension of at least 5 Anstroms and a silica:alumina ratio of at least 30:1 and which is a large pore zeolite or zeolite having a Constraint Index of 1 to 12, which comprises calcining the zeolite containing silver cations at a temperature of 540° to 900° C. after which the calcined zeolite is subjected to reducing treatment.

16. A method according to claim 15 in which the treated zeolite is calcined at a temperature of 750° to 875° C.

17. A method according to claim 15 in which the zeolite has a Constraint Index of 1 to 12 and a silica:alumina ratio of at least 40:1.

18. A method according to claim 17 in which the zeolite is ZSM-5.

19. A method according to claim 17 in which the content of silver cations is at least 0.1 weight percent.

20. A method according to claim 18 in which the content of silver cations is at least 0.5 weight percent.

21. A method according to claim 19 in which the content of silver cations is from 0.5 to 10 weight percent.

22. A method according to claim 20 in which the content of silver cations is from 0.5 to 5 weight percent.

23. A method according to claim 17 in which the zeolite is a large pore zeolite.

24. A method according to claim 17 in which the zeolite is zeolite beta.

* * * * *